United States Patent [19]

Mares et al.

[11] Patent Number: 5,358,475
[45] Date of Patent: Oct. 25, 1994

[54] HIGH MOLECULAR WEIGHT BIORESORBABLE POLYMERS AND IMPLANTABLE DEVICES THEREOF

[75] Inventors: Frank Mares, Whippany; Reginald T. Tang, Warren, both of N.J.; Tin-Ho Chiu, Reading, Mass.; Theodore Largman, Morristown, N.J.

[73] Assignee: United States Surgical Corporation, Norwalk, Conn.

[21] Appl. No.: 952,203

[22] Filed: Sep. 28, 1992

Related U.S. Application Data

[60] Continuation of Ser. No. 618,580, Nov. 27, 1990, abandoned, which is a division of Ser. No. 809,978, Dec. 17, 1985, abandoned.

[51] Int. Cl.⁵ ............................................. A61F 2/54
[52] U.S. Cl. ......................................... 623/66; 623/12; 606/152; 523/113; 528/354
[58] Field of Search ............... 623/11, 12, 16, 66; 528/272, 354, 302, 303; 523/113, 114, 115; 606/152

[56] References Cited

U.S. PATENT DOCUMENTS

| | | | |
|---|---|---|---|
| 3,463,158 | 8/1969 | Schmitt et al. | 623/66 X |
| 3,786,817 | 1/1974 | Palma | 128/334 R |
| 4,452,973 | 6/1984 | Casey et al. | 528/354 |
| 4,534,349 | 8/1985 | Barrows | 128/334 C X |
| 4,565,789 | 1/1986 | Liotta et al. | 436/501 X |
| 4,643,734 | 2/1987 | Lin | 623/16 |
| 4,819,263 | 1/1990 | Kotliar et al. | 606/230 |
| 4,916,193 | 4/1990 | Tang et al. | 606/230 |
| 5,061,281 | 10/1991 | Mares et al. | 606/152 |

OTHER PUBLICATIONS

Nyilas et al., "Peripheral Nerve Repair with Bioresorbable Prosthesis", *Trans Am Soc Artif Intern Organs* vol. XXIX, Apr. 1983.

*Primary Examiner*—Randall L. Green
*Assistant Examiner*—Paul Prebilic

[57] ABSTRACT

Nerve channels made from high molecular weight lactic acid polymers, preferably polymers having a molecular weight between about 234,000 and 320,000, provide an unexpectedly beneficial effect on cell growth and regeneration of function.

12 Claims, 1 Drawing Sheet

HIGH MOLECULAR WEIGHT BIORESORBABLE POLYMERS AND IMPLANTABLE DEVICES THEREOF

This application is a continuation of application Ser. No. 618,580 filed Nov. 27, 1990, now abandoned which in turn is a divisional of application Ser. No. 809,978 filed Feb. 17, 1985, now abandoned.

FIELD OF THE INVENTION

This invention relates to an improvement in the use of bioresorbable polymers for implantation into living tissue characterized in that a particular molecular weight range is selected that demonstrates an unexpectedly beneficial effect on cell growth and therefore regeneration of function.

BACKGROUND OF THE INVENTION

The use of bioresorbable polymers for implantation in living tissue has steadily increased over the last few decades. Medical applications of such polymers include absorbable sutures, intraosseous implants and slow-release drug delivery systems.

More recently, their use has been extended to microtubular tissue regeneration guidance channels. For example, bioresorbable materials have been used in the repair of injured nerves. Nerves with severed axons, but intact somas, may retain the capability of regrowing from the proximal stump to reconnect distally. Structures have been fabricated that serve as conduits for the regrowth and reconnection of severed nerves. After accomplishing their function, these guides gradually disappear from the host.

To be effective, these devices, commonly known as nerve channels, nerve guidance channels, nerve guidance tubes, nerve guides, or nerve tubes, must be made from materials that meet a wide range of biological and physicochemical prerequisites. The material must be bioresorbable, nontoxic, noncarcinogenic, nonantigenic, and must demonstrate favorable mechanical properties such as flexibility, suturability, and amenability to custom fabrication.

Further, it has been recently appreciated that these materials also must be capable of supporting cellular growth, to the extent that they actually exert a "neurotropic" effect. After exerting such an effect, they must also retain structural integrity to the extent necessary to maximize the number of axons reaching the distal stump to restore nerve function. This requires guidance channel biodegradation/resorption rates compatible with axon growth rates.

Examples of absorbable materials used in nerve repair include collagen as disclosed by D. G. Kline and G. J. Hayes, "The Use of a Resorbable Wrapper for Peripheral Nerve Repair, Experimental Studies in Chimpanzees", *J. Neurosurgery* 21, 737 (1964). However, one of the major disadvantages inherent with collagenous materials is their potential antigenicity.

Two related patents, U.S. Pat. Nos. 4,033,938 and 3,960,152, disclose bioabsorbable polymers of unsymmetrically substituted 1,4-dioxane-2,5-diones which are broadly stated to be useful as tubes or sheets for surgical repair such as nerve and tendon splicing. A similar disclosure in U.S. Pat. No. 4,074,366 relates to poly(N-acetyl-D-glucosamine), i.e. chitin.

Other biodegradable polymers of particular interest for medical implantation purposes are homopolymers and copolymers of the alpha-hydroxy carboxylic acids, glycolic acid and lactic acid. These materials undergo hydrolytic scission to form metabolites normal to the body, which are therefore amenable to resorption.

A biodegradable polyglactin suture mesh shaped as a tube around a nerve defect to serve as a framework for proliferating cells has been reported in *Muscle and Nerve* 5, 54–57 (1982). However, less than satisfactory results were achieved in that some of the regenerating axons gained access to the meshes of the polyglactin tube causing the formation of minifascicles. A nerve cuff in the form of a smooth, rigid tube has also been fabricated from a copolymer of lactic and glycolic acids [*The Hand* 10, (3) 259 (1978)].

U.S. Pat. No. 4,481,353 discloses a bioresorbable polyester terpolymer that also includes an alpha-hydroxy carboxylic acid in conjunction with Krebs cycle dicarboxylic acids and aliphatic diols. These polyesters are useful in fabricating nerve guidance channels as well as other surgical articles such as sutures and ligatures.

Regenerated nerves have also been successfully obtained with nerve guides prepared from the homopolymer poly(DL-lactic acid), as measured by myelinated axon counts. The polymers used were obtained commercially, and had a weight average molecular weight of approximately 68,000, which was fractionated to a maximum weight average molecular weight of 113,000. In some cases, a bioresorbable plasticizer was added to impart flexibility and suturability. Studies conducted with a transected rat optic nerve using the nerve guide have shown that the formation of a cable is induced. The cable is composed of fibroblasts, macrophages, astrocytes, oligodendrocytes, collagen, Schwann cells, a connective tissue sheath and numerous blood vessels and myelinated and unmyelinated axons. *Transactions of the American Society of Artificial Internal Organs,* Vol. 29 (1983) pp. 307–313. Results with similar nerve guides, reported to have an weight average molecular weight of 100,000, are disclosed in *Plastic Reconstructive Surgery* 62, 173 (1984).

However, the art has yet to disclose or suggest the selective use of an alpha-hydroxy carboxylic homopolymer or copolymer in a critical range of molecular weight for implantation into living tissue.

SUMMARY OF THE INVENTION

Apart from merely maintaining the mechanical integrity of the device itself, the present inventors have discovered that the molecular weight of the polymer used also has a marked physiological influence on the growth rate of living tissue, particularly nerve growth. The ability of the tissue to regenerate and even to regain function has been vastly encouraged through the use of a polymer within a specific molecular weight range.

This unexpectedly beneficial biological effect is attributed to a critical molecular weight range of the polymer. Hence, the spectrum of applicability of such bioresorbable polymers involves implants to aid the regeneration of devitalized organs.

It is thus an object of the present invention to provide an improvement for a device that is suitable for implantation into a living organism, characterized in that at least a part of such a device is composed of a bioresorbable polymer of a particular molecular weight range having the capability of encouraging cellular growth and therefore regeneration of function.

It is a further object of the present invention to provide an improvement for a device that is suitable for implantation into a living organism, at least part of such device being composed of a homopolymer or copolymer of alpha-hydroxy carboxylic acids, characterized in that a particular molecular weight range of said polymer is used which has been shown to have the capability of encouraging cellular growth and therefore can encourage regeneration of function.

More particularly, it is an object of the present invention to provide an improvement in the above device by use of the homopolymer poly(DL-lactide) in the weight average molecular weight range of greater than about 150,000, as measured by gel permeation chromatography.

It is yet another object of the present invention to provide an improved nerve channel composed in whole or in part of a bioresorbable polymer that is a homopolymer or copolymer selected from the group consisting of one or more of the alpha-hydroxy carboxylic acids, glycolic acid, L-lactic acid, D-lactic acid, and in particular, DL-lactic acid, characterized in that said nerve channel is capable of encouraging the processes of neuronal growth and regeneration of function.

The above and other objects of the present invention will become apparent when considering the detailed description of the preferred embodiments of the invention which follow.

DETAILED DESCRIPTION OF THE PREFERRED EMBODIMENTS

Figure 1:
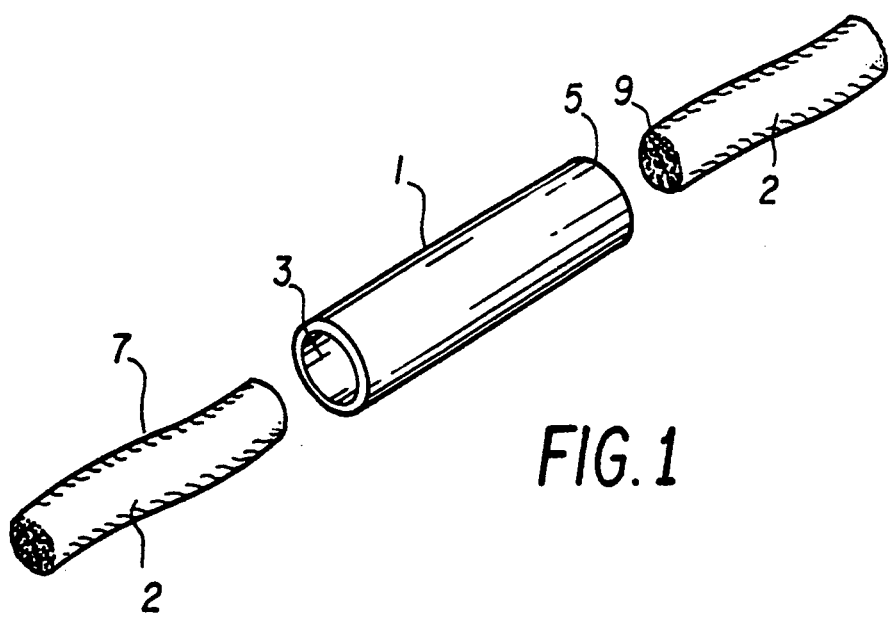
FIG. 1 illustrates the nerve channel embodiment of the present invention for resecting severed ends of a nerve.

The device of the present invention may be fabricated into various forms depending on intended use. Some contemplated forms include solid products such as orthopedic pins, clamps, screws, or plates, clips, staples, vascular implants or supports and nerve channels or supports. Other medical devices could include fibrillar products, knitted, woven or felted such as velours, burn dressings, hernia patches, absorbent papers or swabs, medicated dressings, facial substitutes, gauze, fabric, sheet, felt or sponge for hemostasis, dental packs and breast prostheses. A good description of the formation of bioresorbable materials as matted surgical dressings may be found in U.S. Pat. No. 3,937,223 to Roth. The present improvement could also be useful for bioresorbable polymers in the form of a flake or powder for burns or abrasions, foam, film spray for prosthetic devices, and Slowly digestible ion-exchange resins and slow release devices in the form of pills or pellets.

Particularly useful are tubes of varying shapes, lengths and diameters, to be implanted temporarily or permanently. Of these tubular protheses may be mentioned vascular and nerve guidance channels and the like. In the case of the nerve guidance channel, the particular configuration of such tubes may vary according to the size and shape of the nerve to be repaired, and whether the intended repair is to take place in human surgery or in surgery involving other animal species.

With respect to nerve guidance channels, U.S. Pat. No. 3,833,002 to Palma discloses various sizes and shapes that may be employed. Lengths of the tubes, internal diameters, and tubular wall thicknesses may vary according to intended use. The length of the tube would ordinarily be commensurate with the size of the gap to be repaired, also allowing extra tubing in which to insert nerve stumps. The present inventors have found that particularly useful internal diameters commonly range from 0.013 mm to 5.00 mm. It is also desirable to obtain tubes whose wall thicknesses fall within a specific range, such as 0.08 mm to 3.0 mm. A preferred range is 0.5 mm to 1.5 mm in thickness.

The bioresorbable polymers of the invention include homopolymers and copolymers of one or more of the alpha hydroxy carboxylic acids, such as glycolic acid, L-lactic acid, D-lactic acid, or DL-lactic acid. Preferred polymers include homopolymers of the lactic acid monomers, most preferred being DL-lactide.

As used herein, the term "polylactide" is equivalent to "poly (lactic acid)" as meaning a polymer of lactic acid. In particular, DL-lactide is a lactide derived from a roughly racemic mixture of lactic acid, and this nomenclature is interchangeable with (DL) lactic acid. Similarly, the terms polyglycolide and poly (glycolic acid) are equivalent.

To achieve beneficial biological effects, the desired weight average molecular weight range of the polymer is greater than about 150,000. A preferred range is about 150,000–500,000. More preferred is a range of about 175,000–350,000. Most preferred is a molecular weight range of about 200,000–250,000.

The polymerization process should be carried out in such manner as to achieve the desired polymer molecular weight range. For example, in the case of polylactide, polymerization of the monomeric lactide units can be effected by any acceptable process, such as by using ring opening polymerization, and the like. It is preferred to use a melt polymerization procedure with stannous octoate as the polymerization catalyst, as it is postulated that the polymer molecular weight increases and molecular weight distribution decreases with its use. When using stannous octoate as the catalyst, the requisite parts per million (ppm) range from about 5 to about 800. A preferred amount is about 75 ppm −200 ppm. Reaction time ranges from about 4 hours to about 168 hours, with 6 hours being preferred Reaction temperatures range from about 75° to 240° C., with about 180° C. being preferred.

To obtain polymers of different molecular weight, fractional precipitation of the polymer can be achieved using a "good-solvent" such as chloroform or dioxane and a "non-solvent" such as water, methanol, or the like. Polymers of narrow molecular weight distribution are also obtainable in this manner.

Polymers are generally polydisperse or heterogeneous in molecular weight. To improve the physical properties of a polymer product, it is thus desirable to control the molecular weight distribution by the use of fractionation. The molecular weight distribution is commonly calculated as a dispersity number, which is the weight average molecular weight divided by the number average molecular weight (number of polymer units of a particular molecular weight). Dispersity of a polymer for use in implantation devices is preferred to be less than about 10.0; more preferred is a dispersity number of less than about 3.0; most preferred is 1.0–1.9.

Further, polymers of different weight average molecular weights and distribution could be judiciously combined to obtain a material of desired weight average molecular weight and distribution.

A biocompatible plasticizer or plasticizers may be added to impart greater flexibility to the finished device. Such plasticizers include, e.g., but are not limited to, acetyl tributyl citrate, acetyl triethyl citrate, tri-n-butyl citrate, triethyl citrate, and triacetin. In particular, bioresorbable triethyl citrate has been found to be useful.

The polymeric materials of the present invention may also be used in conjunction with biodurable materials. Such a construction may serve as a means of extending the in vivo longetivity of a particular implant. It is contemplated that a composite may be formed by the use of a mixture, or a coating film, or layer, or the like of the bioresorbable polymers of the specific molecular weight range and of a suitable molecular weight distribution with one or more biodurable materials such as silicon, silicon rubber, polyethylene, polyethylene terephthalate, polyfluoroethylene, polyphosphazene, polyurethane, segmented polyurethane, or the like. For some applications, such as the nerve channel, it is preferred that the bioresorbable material form a continuous medium of the device.

The desired devices may be formed from the polymer by any suitable means including solution formation or heat formation. In general, standard polymer processing techniques can be used to fabricate devices for implantation into living tissue. Hygenic and clean-room conditions for manufacturing of medical articles should be followed. For example, when solution formation is utilized, polymer solutions are commonly filtered before use in a laminar-flow hood to insure that the devices are prepared under clean-room conditions.

The devices of the present invention may also include the addition of "tropic factors" desirable for the growth and survival of various classes of cells in tissue culture, these factors most often being macromolecular proteins. Of particular interest are neuronotrophic factors. Of these growth factors may be mentioned such substances as collagen, fibrinogen, fibronectin, and laminin.

The devices of the present invention may also be sterilized by means of the techniques usually employed by surgery as long as extensive decomposition of the material does not result. For example, sterilization with ethylene oxide at room temperature may be employed.

The following examples illustrate certain preferred embodiments of the invention and are not definitive of scope.

POLYMER PREPARATION EXAMPLE I

A catalyst solution containing 2.49 mg/ml of stannous octoate dissolved in THF was prepared. Two mls of the stannous octoate solution was added to 25 g of DL-lactide to achieve 200 parts per million. This mixture was then heated under an inert atmosphere for 6 hours at 180° C. The molecular weight average of the resulting polymer was determined to be approximately 178,000 in the absence of solvent weight. Molecular weight was determined by gel permeation chromatography, calibrated against polystyrene standards in THF.

POLYMER PREPARATION EXAMPLE II

Preparation of high molecular weight poly(DL-lactide) was effected as follows.

Seventy four grams of recrystallized DL lactide was charged to a Teflon ® reactor along with 74 μl of 10% stannous octoate in toluene. The reactor was fitted with a nitrogen inlet, thermocouple and an anchor stirrer. The vessel contents were heated by means of an oil bath. A Servodyne gauge and chart recorder were used to monitor the viscosity of the polymer melt.

After stirring for 70 minutes under a nitrogen blanket, the viscosity rose rapidly. The oil bath temperature was held at 190°–200° C. for five hours while the internal thermocouple registered 155° C.

A 30 g aliquot of the polymer was dissolved in acetone and then precipitated with water in a Waring blender. The recovered solids were washed thoroughly with methanol and further granulated in a Waring blender. Finally, the solids were dried in a vacuum oven for 2 days at room temperature, and 24 g of polymer were recovered. Reduced viscosity of the polymer was ηsp/c 2.10, 0.1% in dioxane.

The molecular weight average was determined by gel permeation chromatography to be approximately 207,000 in the absence of solvent weight.

Polymers of various molecular weights and distribution were obtained by fractional precipitation.

IMPLANTATION DEVICE PREPARATION EXAMPLE I

Nerve channels composed of polymers prepared substantially as above, ranging in molecular weight from about 177,000 to about 320,000, were readily prepared by the usual multiple solution dipping method using inert metal mandrels or glass mandrels for dipping. Polymer with a weight average molecular weight normally of about 90,000 was obtained commerically (Polyscience). Nerve channels were then prepared from a fractionation, with a weight average molecular weight of 113,000, to serve as a comparison. A THF solution of the polymer was normally used with a plasticizer. Polymer solutions were filtered in a laminar-flow hood before use.

Alternatively, the standard method of melt extrusion of polymers Was applied to these polymers to obtain tubings of the desired size.

In either case, clean-room conditions were maintained during the preparation of the nerve channels.

FIG. 1 illustrates a perspective view of a nerve guidance channel prepared according to the present invention, into which severed nerve ends may be inserted. Shown therein is a cylindrical nerve guidance tube 1 having open opposite ends 3 and 5 into which severed distal nerve end 7 and severed proximal nerve end 9 may be inserted. After the nerve ends are inserted into the tube, they may be surgically sutured in place with sutures commonly available.

IMPLANTATION STUDIES

A. Mouse Sciatic Nerve Regeneration

Figure 2:
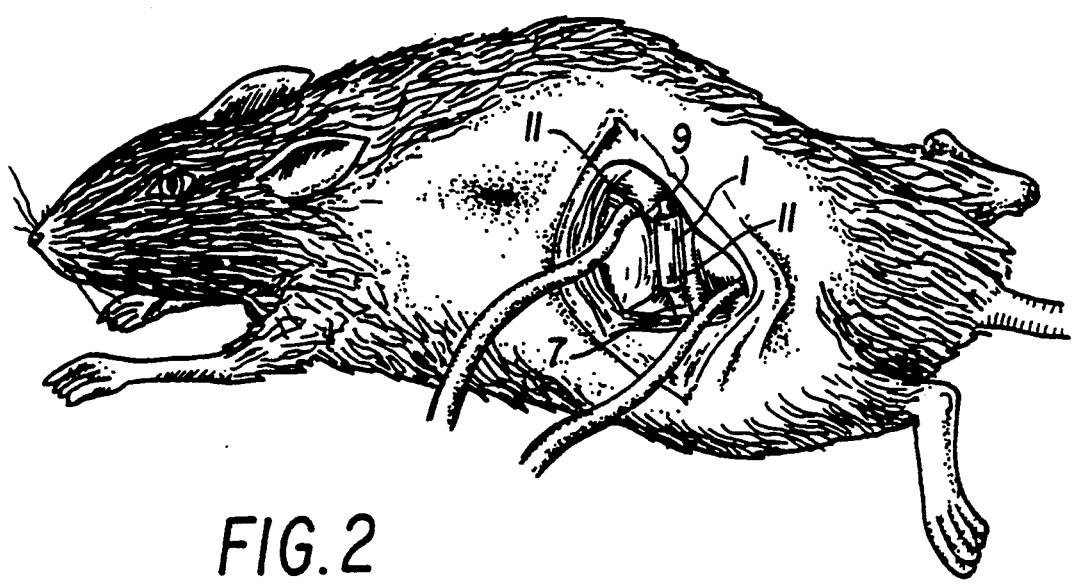
FIG. 2 is a laboratory animal with a nerve channel bridging a severed sciatic nerve, used in nerve regeneration studies.

FIG. 2 further illustrates the experimental design of the mouse sciatic nerve regeneration study. Therein is shown an adult anesthetized C57BL/6J mouse with a sciatic nerve 2 transected and with nerve guide 1 in place. In each mouse, both the proximal stump 9 and distal stump 7 (detailed in FIG. 1) were secured by a single 10-0 nylon suture 11 and were inserted into a 5-6 mm length of nerve guide tube 1 to give a final gap length of 3–4 mm. The tubes were composed of poly (DL-lactide) of molecular weights of about 177,000, 234,000, or 320,000. Poly (DL-lactide) tubes with a molecular weight of approximately 113,000 were inserted into other mice for comparison purposes. At 2, 4 or 6 weeks postoperatively, the sciatic nerve of the animal, appropriately perfused for tissue studies, was again exposed and retransected 3 mm distal to the nerve guide tube. Nerve guides with enclosed regenerated nerves were then dissected out, post-fixed in 2% osmium tetroxide and processed for plastic embedding (DER, Ted Pella Inc.). Just before embedding, the tissue was divided into several segments for sampling at multiple cross-section levels. For most implants, five levels were sampled by one micron sections. These levels were: proximal sciatic stump at 1 to 2 mm proximal to the implant; three levels- (proximal, central, distal) within the tube 1 through the original gap, and the distal stump 1 to 2 mm distal to the implant. Data obtained in the central section was used for comparison. The number of myelinated axons in these sections was determined with a computer-control system. Selected blocks were then resectioned for electron microscopy.

The following table summarizes the myelinated axon count of regenerated sciatic nerve (through the 3-4 mm gap) of the study:

| Polymer (MW) | 2 Week | 4 Week | 6 Week |
| --- | --- | --- | --- |
| 113K | 0 | 304 ± 102 (N = 5) | 627 ± 185 (N = 5) |
| 177K | 0 | 827 ± 188 (N = 5) | 759 ± 512 (N = 4) |
| 234K | 0 | 1457 ± 124 (N = 3) | 1844 ± 429 (N = 5) |
| 320K | 0 | 821 ± 416 (N = 3) | 1637 ± 418 (N = 5) |

K = MW × 1000
N = No. of animals

What is claimed is:

1. In a nerve channel suitable for implantation into a living organism and in the form of a tube, the improvement which comprises that at least a portion of said nerve channel is comprised of a homopolymer of poly(DL-lactide) having an average molecular weight of between about 234,000 and 320,000.

2. A nerve channel comprising a tube comprising a polymer consisting essentially of lactice acid ester linkages said polymer having an average molecular weight between about 234,000 and 320,000.

3. The nerve channel of claim 2 wherein the polymer has a narrow molecular weight distribution characterized by a dispersity number of less than about 10.0.

4. The nerve channel of claim 2 wherein the polymer has a narrow molecular weight distribution characterized by a dispersity number of less than about 3.0.

5. The nerve channel of claim 2 wherein the polymer has a narrow molecular weight distribution characterized by a dispersity number in the range of about 1.0 to about 1.9.

6. The nerve channel of claim 2 wherein at least one biocompatible plasticizer is included in the polymer.

7. The nerve channel of claim 2 wherein the nerve channel further comprises one or more biodurable materials.

8. The nerve channel of claim 1 wherein the polymer has narrow molecular weight distribution characterized by a dispersity number of less than about 10.0.

9. The nerve channel of claim 8 wherein the dispersity number is less than about 3.0.

10. The device of claim 1 wherein the bioresorbable polymer is the homopolymer poly (DL-lactide).

11. The nerve channel of claim 1 wherein at least one biocompatible plasticizer is included in the polymer.

12. The nerve channel of claim 1 wherein the bioresorbable polymer is mixed with one or more biodurable materials.

* * * * *